(12) United States Patent
Petrie

(10) Patent No.: US 6,312,593 B1
(45) Date of Patent: Nov. 6, 2001

(54) ULTRAVIOLET BLOOD IRRADIATION CHAMBER

(76) Inventor: Thomas R. Petrie, 132 Deerhaven La., Newfoundland, NJ (US) 07435

( * ) Notice: Subject to any disclaimer, the term of this patent is extended or adjusted under 35 U.S.C. 154(b) by 0 days.

(21) Appl. No.: 09/299,241

(22) Filed: Apr. 23, 1999

(51) Int. Cl.[7] ........................................................ A61L 2/10
(52) U.S. Cl. ......................... 210/205; 250/437; 604/6.08; 607/94
(58) Field of Search ................................. 210/748, 198.1, 210/205; 250/432 R, 435, 437, 438; 422/186.3; 607/94; 604/6.08

(56) References Cited

U.S. PATENT DOCUMENTS

| | | | |
|---|---|---|---|
| 1,683,877 | * | 9/1928 | Edblom et al. . |
| 2,308,516 | * | 1/1943 | Knott . |
| 2,309,124 | * | 1/1943 | Knott . |
| 4,676,896 | * | 6/1987 | Norton ............................ 210/192 |
| 4,876,014 | * | 10/1989 | Malson ............................ 210/748 |
| 5,133,932 | * | 7/1992 | Gunn et al. ...................... 422/24 |
| 5,433,738 | * | 7/1995 | Stinson ............................ 607/92 |
| 5,868,695 | * | 2/1999 | Wolf, Jr. et al. . |

* cited by examiner

Primary Examiner—David A. Simmons
Assistant Examiner—Frank M. Lawrence
(74) Attorney, Agent, or Firm—Charles W. Calkins, Esq.; Kilpatrick Stockton LLP

(57) ABSTRACT

An irradiation chamber adapted to treat a blood stream infection by subjecting the stream to ultraviolet radiation. The chamber is provided with a window transparent to UV rays under which is an array of parallel baffle plates that define a series of interconnected channels forming a labyrinthine passage extending from the inlet to the outlet of the chamber. Each baffle plate includes a transverse protuberance which intercepts the flow of blood in the related channels to produce a Bernoulli distortion acting to agitate the blood stream. And each baffle plate is vertically tapered to induce blood from the lower regions of the stream within the channels to rise to the upper region adjacent the window. As a consequence of these internal displacements within the flow stream and the intermingling of blood regions in the course of its flow through the labyrinthine passage, all portions of the blood stream are adequately exposed to UV rays.

8 Claims, 1 Drawing Sheet

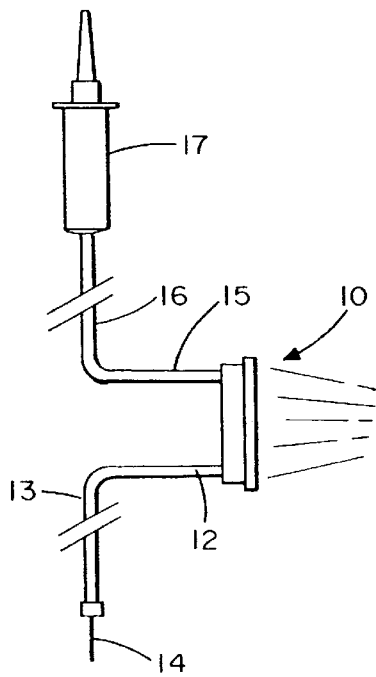
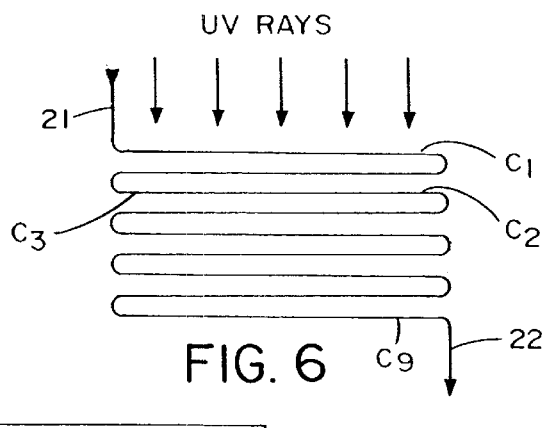
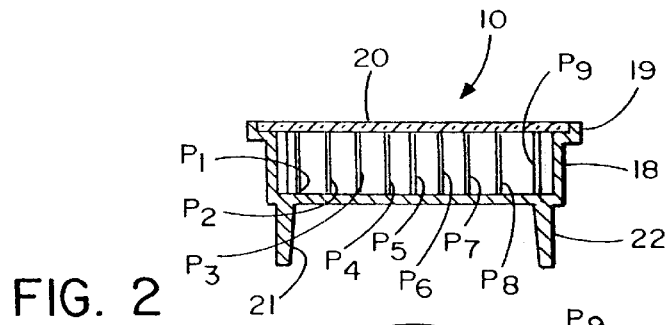
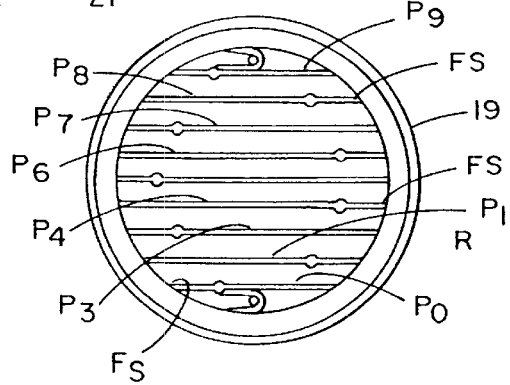
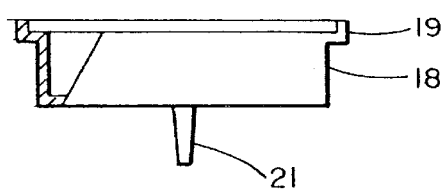
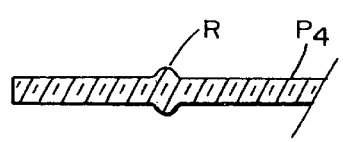
FIG. 1
FIG. 2
FIG. 3
FIG. 4
FIG. 5
FIG. 6

ULTRAVIOLET BLOOD IRRADIATION CHAMBER

RELATED APPLICATION

This regular patent application is related to applicant's provisional application No. 60/082,950, filed Apr. 24, 1998, entitled "CHAMBER WITH INPUT AND OUTPUT PORTS AND SMALL INTERRUPTER PADS WHICH ARE USED TO IMPART A GENTILE AGITATION AND FLOW OF BLOOD THROUGH THE CHAMBER WHICH IS BEING EXPOSED TO UV LIGHT." The entire disclosure of this provisional application is incorporated herein by reference.

BACKGROUND OF INVENTION

1. Field of Invention

This invention relates generally to an irradiation chamber wherein a stream of infected blood flowing through the chamber is exposed to ultraviolet radiation to destroy microorganisms carried by the stream, and more particularly to a chamber of this type in which the blood stream flows through a labyrinthine passage which acts to create internal displacements within the blood stream to ensure that all portions thereof are adequately exposed to radiation.

2. Status of Prior Art

Blood, the circulating fluid of the human organism, is an aqueous solution of protein salts and organic substances containing various types of cells and cell products in suspension. The fluid portion of blood is its plasma, whereas the cells and cell products constitute the solid portion.

It is known to treat blood stream infections by subjecting the stream to ultraviolet radiation, for UV rays have bactericidal properties that are effective against the microorganisms responsible for the infection.

Of prior art interest in regard to such treatment is the blood irradiation chamber disclosed in an article by E. K. Knott in the August 1948 issue (Vol. LXXVI-No.5) of the American Journal of Surgery, entitled "Development of Ultraviolet Blood Irradiation."

The circular chamber disclosed in this article whose approximate dimensions are 2 inches in diameter and one inch in thickness, includes a quartz window transparent to UV, under which are baffle plates that fit flush against the window. These baffle plates are arranged to define a labyrinthine passage which snakes from the inlet to the outlet of the chamber.

The baffle plates which are in parallel relation create a series of interconnected flow channels, so that in the course of flow the stream passes around the end of each channel into the next channel in the series.

The circuitous path of the blood stream produces some degree of turbulence as the stream flows through this path, and causes the blood to flow towards and away from the quartz window. It also acts to minimize the creation of regions in the chamber in which there are stagnant pools of blood.

In a Knott irradiation chamber, the quartz window is transparent to UV rays in the range of 1400 to 4000 Angstroms. The function of the chamber is to expose to the stream of blood coursing through its passage to UV rays for a period sufficient to destroy the microorganisms responsible for the infection, but without damaging the cells and cell products in the blood.

Ideally, in a Knott chamber, there should be uniform exposure to UV radiation of each fraction of the blood flowing therethrough so that no portion of the stream remains inadequately treated. But the Knott chamber falls short of this ideal, as a consequence of which the treated blood will not be infection free.

Also of prior art interest are the following patents which show Knott-type blood chambers U.S. Pat. Nos. 2,309,124; 2,308,516; 2,314,281.

SUMMARY OF INVENTION

In view of the foregoing, the main object of this invention is to provide an irradiation chamber adapted to treat a blood stream infection by subjecting the stream to ultraviolet radiation.

More particularly, an object of this invention is to provide a chamber of the above type in which the stream of infected blood coursing through the chamber is internally displaced within the stream whereby substantially all portions of the stream are fully exposed to UV rays.

A significant advantage of a chamber in accordance with the invention is that is useable for the treatment of bacterial and other infections which are not responsive to antibiotics or anti-viral agents, or for the treatment of patients who are allergic to antibiotics or anti-viral agents.

Yet another object of the invention is to provide a disposable chamber of the above type which is fabricated of low cost synthetic plastic material, and which can be discarded after a single use, thereby dispensing with the need to clean and sterilize the chamber after use.

Briefly stated these objects are attained in an ultraviolet blood irradiation chamber adapted to treat a blood stream infection by subjecting the stream to ultraviolet radiation. The chamber is provided with a window transparent to UV rays under which is an array of parallel baffle plates that define a series of interconnected channels forming a labyrinthine passage extending from the inlet to the outlet of the chamber.

Each baffle plate includes a rounded transverse protuberance which intercepts the flow of blood in the related channels to produce a Bernoulli distortion acting to agitate the blood stream. And each baffle plate is vertically tapered to induce blood from the lower regions of the stream within the channels to rise to the upper region adjacent the window. As a consequence of these internal displacements within of the flow stream in the course of its flow through the labyrinthine passage, all portions of the blood stream are adequately exposed to UV rays.

BRIEF DESCRIPTION OF DRAWINGS

For a better understanding of the invention, as well as other objects and features thereof, reference is made to the accompanying drawings wherein;

FIG. 1 illustrates a blood treatment system that includes an irradiation chamber in accordance with the invention;

FIG. 2 is a section taken thorough the diametrical plane of the chamber;

FIG. 3 is a plan view of the chamber with its window removed;

FIG. 4 shows one of the baffle plates in the chamber;

FIG. 5 is a longitudinal section taken trough one of the plates; and

FIG. 6 illustrates the labyrinthine flow passage through the chamber.

DESCRIPTION OF INVENTION

Referring now to FIG. 1, there is shown a system for treating an infected blood stream, which system includes an irradiation chamber 10 in accordance with the invention which is exposed to a source 11 of ultraviolet radiation. The inlet port 12 of chamber 10 is coupled by a line 13 to a hypodermic needle 14 which is injectable into the arm of a patient for withdrawing infected blood from the patient.

The stream of the patient's blood passing through chamber 10 is exposed to ultraviolet rays emanating from source 11 to destroy the infectious microorganism carried by the blood. The treated blood which is discharged from the outlet port 15 of the chamber is fed by a line 16 to an IV set 17, so that the purified blood can be returned to the patient.

The system disclosed in FIG. 1 is merely by way of example. Thus in practice the blood to be treated can be fed into the chamber by means of a controlled pump adapted to feed the blood into the chamber at a predetermined constant flow rate. And UV-source 11 may take the form of a controlled UV generator yielding UV rays having a desired intensity.

It must be pointed out that the intensity of the UV radiation must be such that the rays are strong enough to destroy the microorganisms carried by the blood, but of insufficient intensity to damage the cells and cell products included in the blood stream.

Thus the parameters of the system in regard to blood flow rate and UV intensity must be tailored to the infected blood being treated and the nature of this infection.

As illustrated in FIGS. 2 to 5, chamber 10 includes a dish-shaped container 18 having an annular rim 19, the container being molded of polypropylene or other high-strength, synthetic plastic material that is sterile and has acceptable medical properties.

Seated within rim 19 is a disc-shaped window 20 that is transparent to UV radiation and is bonded to the rim to seal the chamber. Window 20 may be composed of silica, quartz or other material having a UV transmission band of 200 to 400 nm.

Projecting from the base of container 18 and communicating with its interior are an inlet port 21 and an outlet port 22, the ports being at diametrically opposed positions. These ports are tapered to accommodate fittings of flexible tapered tubing and thereby prevent distortion of the fluid flow.

Molded within container 18 is an array of nine equi-spaced parallel baffle plates $P_1$ to $P_9$. These plates define a series of interconnected fluid channels creating a labyrinthine or serpentine path running from inlet port 21 to outlet port 22.

As shown in FIG. 3, each baffle plate extends from one end of the circular container 18 to which it is joined to a point displaced from the opposing end of the container to create a free space FS through which fluid is free to pass from one channel to the adjacent channel. These free spaces are in staggered relation so that fluid flowing through one channel makes a turn through the free space to pass into the adjacent channel, and when it comes to the end of the adjacent channel, it then makes a turn to pass into the next channel and so on.

As shown in FIG. 6, the resultant flow passage formed by interconnected channels $C_1$ to $C_9$ is labyrinthine, as a consequence of which the fluidic flow through the passage is non-laminar and somewhat turbulent, thereby agitating the stream.

However, as previously noted, in order that the blood stream passing through the chamber is fully exposed so that all portions of the stream are subjected to UV rays, it is necessary that in the course of its passage through the chamber each and every region of the stream is brought into proximity of the window through which the rays are conveyed.

Otherwise if portions of the blood stream in the lower regions of the stream in the course of their passage through the chamber are never brought near the window, then these portions will not be adequately irradiated, for the blood cells and cell products in the upper region of the stream that is next to the window will effectively block the rays and prevent their reaching the lower regions.

In order therefore to stimulate actions producing internal displacements of the blood stream in the course of its passage through the chamber that cause the portions of the stream to intermingle so that lower region portions find their way to the upper region for exposure to UV radiation, a chamber in accordance with the invention includes the following features.

Feature I:

As shown in connection with FIGS. 3 and 5, each baffle plate $P_1$ to $P_9$ at an end position adjacent its free space FS is provided with a transverse protuberance or ridge R, that is rounded. This broad bump on the surface of the baffle plate at both sides thereof acts to intercept the fluid flowing over the surface of the side to produce a Bernoulli distortion, an effect which causes the fluid when it passes over the bump to roll over or to spiral, thereby agitating the stream.

Bernoulli's principle of hydrodynamics states that within a fluid under conditions of steady flow in which the pressure and velocity at any one point remains constant, then the sum of the energy of velocity, the energy of pressure, and the potential energy of elevation remains constant. The term of this equation are upset by the bump in the path of fluid flow, for the velocity of fluid passing over the bumps is greater on the far side of the bump and will impart a roll to the fluid and cause it to spiral, thereby agitating the stream.

Feature II:

It will be seen in FIG. 2 that each baffle plate ($P_1$ to $P_2$) becomes progressively narrower as one goes from the base to the upper edge of the plate abutting window 20, thereby vertically tapering the plate. The effect of this taper is to induce lower regions of the blood stream to travel toward the upper region of the stream under the window and thereby become exposed to the UV radiation. The internal displacements of the lower regions of the blood stream in the upward direction are promoted by the spiralling of the stream caused by protuberance R.

Thus the upper and lower regions of the blood stream are caused to intermingle as the stream flows through the labyrinthine passage in the chamber, and no portion of the stream remains unexposed to UV radiation. This make it feasible to use a lower intensity of UV radiation than is necessary in a Knott chamber where a higher intensity is required to penetrate the lower regions of the blood stream to disinfect these regions.

It must again be stressed that an excessive intensity of UV radiation may adversely affect the cells and cell products in the blood stream, and that for proper disinfection, the UV intensity must be such that only the microorganisms are destroyed.

While there has been shown and described a preferred embodiment of an ultraviolet blood irradiation chamber in accordance with the invention, it will be appreciated that many changes may be made thereon without departing from the spirit of the invention.

I claim:

1. A chamber for subjecting a stream of infected blood flowing through the chamber to ultraviolet radiation to destroy microorganisms responsible for the infection; said chamber comprising:

A. a container having an inlet port and an outlet port and a surface formed by a window transparent to ultraviolet rays;

B. an array of parallel baffle plates disposed within the container to define a series of flow channels which are interconnected by free spaces at alternate ends of the plates in the array to create a labyrinthine flow passage running from the inlet port to the outlet port; and C. a transverse bump on either side of each of said plates adjacent the free-space end thereof, said bump acting to agitate the blood stream flowing over the bump to intermingle blood in lower regions of the stream with blood in a higher region thereof adjacent the window whereby blood from the lower regions and the higher region are exposed to ultraviolet rays transmitted through the window, wherein each of said baffle plates is progressively tapered to induce blood from said lower regions to travel to said higher region.

2. A chamber as set forth in claim 1, in which said container is dish-like and has an annular rim in which said window is seated.

3. A chamber as set forth in claim 2 in which said window is disc-shaped and bonded to the rim.

4. A chamber as set forth in claim 3 in which the window is formed of silica.

5. A chamber as set forth in claim 1, in which the container and the baffle plates are molded of synthetic plastic material.

6. A chamber as set forth in claim 5, in which the material is polypropylene.

7. A chamber as set forth in claim 6, in which the inlet and outlet ports project from the base of the container.

8. A chamber as set forth in claim 7, in which the ports are tapered.

* * * * *